United States Patent [19]

Rottmaier et al.

[11] 4,433,085
[45] Feb. 21, 1984

[54] TRIAZOLIDINE-3,5-DIONE/FORMAL-DEHYDE/AMINE CONDENSATES AND COMPOSITIONS THEREOF

[75] Inventors: Ludwig Rottmaier, Odenthal; Rudolf Merten, Leverkusen, both of Fed. Rep. of Germany

[73] Assignee: Bayer Aktiengesellschaft, Leverkusen, Fed. Rep. of Germany

[21] Appl. No.: 278,860

[22] Filed: Jun. 29, 1981

[30] Foreign Application Priority Data

Jul. 21, 1980 [DE] Fed. Rep. of Germany ....... 3027582

[51] Int. Cl.$^3$ ..................... C07D 403/04; C08K 5/34; C08K 5/35
[52] U.S. Cl. ..................... 524/83; 524/98; 524/100; 524/106; 260/239.3 R; 548/264; 544/82; 544/132; 544/207; 544/60; 544/194; 544/296; 544/300; 544/357; 544/359; 544/366; 546/187; 546/210; 524/97; 524/99; 524/101; 524/104; 524/96
[58] Field of Search .................. 548/264; 260/239.3 R; 544/82, 132, 198, 207, 60, 194, 296, 300, 357, 359, 366; 524/96, 97, 98, 100, 106; 546/187, 210

[56] References Cited

FOREIGN PATENT DOCUMENTS 2936842  3/1980  Fed. Rep. of Germany .
1330401  5/1963  France .

OTHER PUBLICATIONS

Zinner et al., "Arch. Pharm.", vol. 299, No. 1, pp. 81–91, (1966).
Zinner et al., "Arch. Pharm.", vol. 299, No. 5, pp. 411–417, (1966).

*Primary Examiner*—Robert T. Bond
*Attorney, Agent, or Firm*—Connolly and Hutz

[57] ABSTRACT

A triazolidine-3,5-dione/formaldehyde/amine condensate is disclosed of the formula

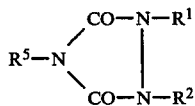

in which
  wherein the terms $R^1$, $R^2$ and $R^5$ are defined hereinafter in the specification
  a process for the preparation of such condensate by reaction of a triazolidine-3,5-dione with formaldehyde and a suitable nitrogen compound and the use of the condensate as a flame-proofing agent for thermoplastics, especially polyamide and as an auxiliary for modifying polymeric substances.

18 Claims, No Drawings

TRIAZOLIDINE-3,5-DIONE/FORMALDEHYDE/AMINE CONDENSATES AND COMPOSITIONS THEREOF

The present invention relates to optionally substituted triazolidine-3,5-dione/formaldehyde/amine condensates and processes for their preparation.

The new triazolidine-3,5-dione/formaldehyde/amine condensates of the formula

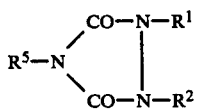

(I)

in which
$R^1$ and $R^2$ independently of one another represent hydrogen, alkylcarbonyl or

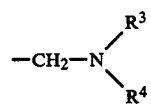

wherein
$R^3$ denotes hydrogen, alkyl, cycloalkyl, aralkyl, aryl or a heterocyclic radical and
$R^4$ denotes alkyl, alkenyl, aralkyl, aryl, a heterocyclic radical, alkylcarbonyl, alkenylcarbonyl or alkoxycarbonyl,
or wherein
$R^3$ and $R^4$, together with the nitrogen atom of which they are substitutents, can denote a nitrogen-heterocyclic radical which optionally contains other hetero-atoms, and
$R^5$ represents alkyl, cycloalkyl, aralkyl, aryl, alkylcarbonyl or the group

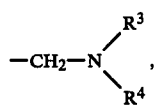

in which
$R^3$ and $R^4$ have the meaning given, or
$R^5$ represents the group

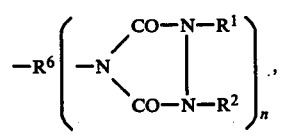

in which
$R^6$ represents a (n 30 1)-valent aliphatic, cycloaliphatic, araliphatic or aromatic radical,
$R^1$ and $R^2$ have the meaning given and
n denotes the number 1 or 2, or
$R^5$ represents the group

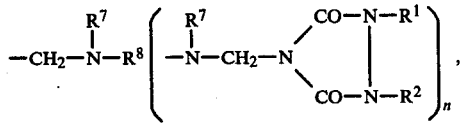

in which
$R^7$ denotes hydrogen, alkyl, cycloalkyl, aralkyl, aryl, a heterocyclic radical or

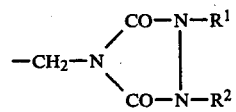

$R^8$ denotes a (m+1)-valent aliphatic, cycloaliphatic, araliphatic, aromatic or heterocyclic radical,
$R^1$ and $R^2$ have the meaning given and
m denotes the number 0, 1 or 2, a hydrogen atom occurring instead of the radical in brackets if m=0 and it being possible for $R^8$ additionally to be a carbonyl group if m=1,
the formula given containing at least one group

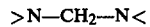

$$>N-CH_2-N<$$

arising from formaldehyde/amine condensation, have been found,

Alkyl radicals which may be mentioned as examples are straight-chain or branched aliphatic radicals with 1 to 20, preferably 1 to 8 and particularly preferably 1 to 4, carbon atoms, such as methyl, ethyl, propyl, isopropyl, butyl, isobutyl, hexyl, octyl, dodecyl, stearyl and eicosyl.

Alkenyl radicals which may be mentioned as examples are straight-chain or branched unsaturated hydrocarbon radicals with 2 to 20, preferably 2 to 8 and particularly preferably 2 to 4, carbon atoms, such as vinyl, propenyl, butenyl, hexenyl, octenyl, dodecenyl, hexadecenyl or eicosenyl.

Cycloalkyl radicals which may be mentioned as examples are cycloaliphatic radicals with 3 to 10, preferably 5 to 6 and particularly preferably 6, carbon atoms, such as cyclopropyl, cyclobutyl, cyclopentyl, cyclohexyl, cyclooctyl and cyclodecyl.

Aralkyl radicals which may be mentioned as examples are hydrocarbon radicals with up to 2 carbon atoms in the aliphatic part and up to 14 carbon atoms in the aromatic part, such as benzyl, α-phenyl-ethyl, β-phenyl-ethyl, 1-naphthyl-methyl, 2-naphthyl-methyl, naphthyl-ethyl, anthryl-methyl, anthryl-ethyl, biphenyl-methyl and biphenyl-ethyl, preferably benzyl.

Aryl radicals which may be mentioned as examples are aromatic hydrocarbon radicals with 6 to 14 carbon atoms, such as phenyl, naphthyl, anthryl and biphenyl, preferably phenyl.

Heterocyclic radicals which may be mentioned as examples are cyclic radicals which, in addition to carbon atoms, also contain one or more hetero-atoms, such as nitrogen, oxygen or sulphur. In the case where such a ring system contains several hetero-atoms, these can also be different hetero-atoms. Examples here are the radicals derived from the following heterocyclic systems: pyrrolidine, piperidine, pyrazolidine, imidazolidine, oxazolidine, thiazolidine, piperazine, morpholine, thiomorpholine, hydantoin, 5,5-dimethyl-hydantoin, parabanic acid, barbituric acid and cyanuric acid.

Alkylcarbonyl radicals which may be mentioned as examples are aliphatic, saturated hydrocarbon radicals located on a α-carbonyl group, the total number of carbon atoms, including the carbonyl group, being 2 to 20, preferably 2 to 8 and particularly preferably 2 to 4. Examples of these radicals are: acetyl, propionyl, butyryl, hexylcarbonyl, decylcarbonyl, stearyl and eicosanoyl.

Alkenylcarbonyl radicals which may be mentioned as examples are olefinic radicals located on an α-carbonyl group, the total number of carbon atoms, including the carbonyl group, being 3 to 20, preferably 3 to 8 and particularly preferably 3 or 4. Examples of these radicals are: acryl, methacryl, crotonyl, undecylenoyl, 9-octadecenoyl, oleyl, sorbyl, linoleyl and eicosenoyl, preferably acryl and methacryl.

Alkoxycarbonyl radicals which may be mentioned as examples are alkoxy radicals located on a α-carbonyl group, the total number of carbon atoms being 2 to 20, preferably 2 to 8 and particularly preferably 2 to 4. Examples of these radicals are: methoxycarbonyl, ethoxycarbonyl, propoxycarbonyl, butoxycarbonyl, hexyloxycarbonyl, dodecyloxycarbonyl, stearyloxycarbonyl and nonadecyloxycarbonyl.

In the case where two radicals together with the nitrogen atom of which they are substituents can denote a nitrogen-heterocyclic radical which optionally contains other hetero-atoms, the following ring systems formed in this manner may be mentioned as examples: pyrrolidine, pyrazolidine, imidazolidine, oxazolidine, thiazolidine, triazolidine, tetrazolidine, thiodiazolidine, piperidine, piperazine, morpholine and thiomorpholine. Further examples are four-membered or seven-membered heterocyclic rings, such as azacyclobutane or azacycloheptane.

In the case where substituents are (n+1)-valent or (m+1)-valent aliphatic, cycloaliphatic, araliphatic, aromatic or heterocyclic radicals, examples which may be mentioned are derivatives of the said alkyl, cycloalkyl, aralkyl or aryl radicals or of one of the said heterocyclic radicals, in which, in addition to the bond to the ring system of the formula (I) and of the formulae given below which are derived therefrom, n or m further hydrogen atoms are replaced by the radicals in brackets which are given in the formulae. n denotes the number 1 or 2, preferably the number 1. m denotes the number 0, 1 or 2; the preferred range which may be mentioned is the expression o, denoting 1 or 2, which is used below instead of m. In the case where m is 0, a hydrogen atom occurs instead of the radical in brackets in the formula. (n+1)-valent and (m+1)-valent radicals also include, for example, toluylene or one of the groups All the radicals mentioned can in turn be monosubstituted or disubstituted and particularly preferably monosubstituted, by halogen, hydroxyl, C-C$_4$-alkoxy, cyano, amino, C$_1$-C$_4$-alkylamino, bis-(C$_1$-C$_4$-alkyl)-amino, C$_2$-C$_4$-alkoxycarbonyl or C$_1$-C$_4$-alkyl, which can be straight-chain or branched.

Examples of triazolidine-3,5-dione/formaldehyde/amine condensates of the general formula (I) which may be mentioned are those of the formula (II)

in which
R$^1$ and R$^2$ have the abovementioned meaning and
R$^9$ denotes alkyl, cycloalkyl, aralkyl, aryl, alkylcarbonyl or wherein
R$^3$ and R$^4$ have the meaning given,
the formula given containing at least one group $>$N—CH$_2$—N$<$ arising from formaldehyde/amine condensation.

Further examples of compounds of the formula (I) which may be mentioned are those of the formula (III)

in which
R$^1$, R$^2$, R$^6$ and n have the abovementioned scope of meaning,
the formula given containing at least one group $>$N—CH$_2$—N$<$ arising from formaldehyde/amine condensation.

Further examples of compounds of the formula (I) which may be mentioned are those of the formula (IV)

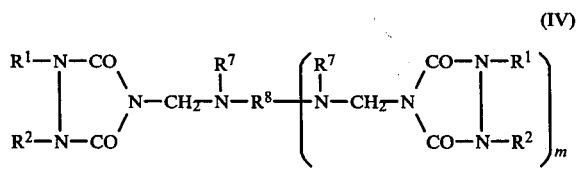 (IV)

in which

R¹, R², R⁷, R⁸ and m have the abovementioned scope of meaning.

Preferred triazolidine-3,5-dione/formaldehyde/amine condensates are those of the formula (V)

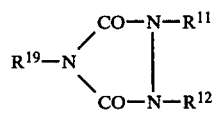 (V)

in which

R¹¹ and R¹² independently of one another denote hydrogen, $C_2$-$C_8$-alkylcarbonyl or

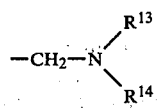

wherein

R¹³ represents hydrogen, $C_1$-$C_8$-alkyl, $C_5$-$C_6$-cycloalkyl, benzyl or phenyl and R¹⁴ represents $C_1$-$C_8$-alkyl, $C_2$-$C_8$-alkenyl, benzyl, phenyl, a heterocyclic radical, $C_2$-$C_8$-alkyl-carbonyl, $C_3$-$C_8$-alkenylcarbonyl or $C_2$-$C_8$-alkoxycarbonyl, or wherein R¹³ and R¹⁴, together with the nitrogen atom of which they are substituents, can denote a nitrogen-heterocyclic radical which optionally contains other hetero-atoms, and R¹⁹ represents $C_1$-$C_8$-alkyl, $C_5$-$C_6$-cycloalkyl, benzyl, phenyl, $C_2$-$C_8$-alkylcarbonyl or

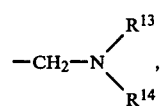

wherein

R¹³ and R¹⁴ have the meaning given, the formula given containing at least one group $$>N-CH_2-N<$$

arising from formaldehyde/amine condensation.

Triazolidine-3,5-dione/formaldehyde/amine condensates of the formula (VI)

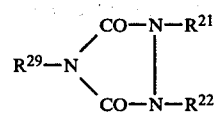 (VI)

in which

R²¹ and R²² independently of one another represent hydrogen, $C_2$-$C_4$-alkylcarbonyl or

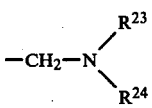

wherein

R²³ represents hydrogen or $C_1$-$C_4$-alkyl and R²⁴ represents $C_1$-$C_4$-alkyl, a heterocyclic radical, $C_2$-$C_4$-alkylcarbonyl or $C_3$-$C_4$-alkenylcarbonyl, or wherein R²³ and R²⁴, together with the nitrogen atom of which they are substituents, can denote a nitrogen-heterocyclic radical which optionally contains other hetero-atoms and R²⁹ denotes $C_1$-$C_4$-alkyl, cyclohexyl, benzyl, phenyl, $C_2$-$C_4$-alkylcarbonyl or

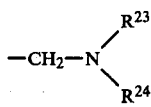

wherein

R²³ and R²⁴ have the meaning given, the formula given containing at least one group $$>N-CH_2-N<$$

arising from formaldehyde/amine condensation, are particularly preferred.

Triazolidine-3,5-dione/formaldehyde/amine condensates of the formula (VII)

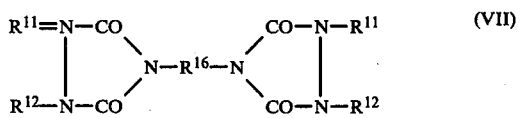 (VII)

in which

R¹¹ and R¹² have the abovementioned scope of meaning and

R¹⁶ denotes alkylene, phenylene, toluylene or one of the groups

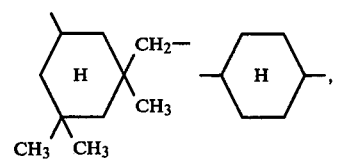

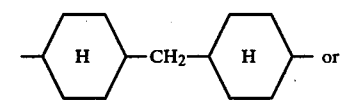

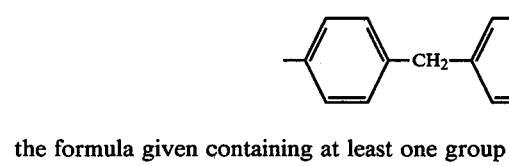

the formula given containing at least one group $$>N-CH_2-N<$$

arising from formaldehyde/amine condensation, are also preferred.

Alkylene radicals which may be mentioned as examples are divalent aliphatic radicals with 1 to 12, preferably 1 to 8 and particularly preferably 2 to 6, carbon atoms, such as methylene, ethylene, trimethylene, tetramethylene, hexamethylene and octamethylene.

Triazolidine-3,5-dione/formaldehyde/amine condensates of the formula (VIII)

$$R^{11}-N-CO\diagdown N-CH_2-N-R^{18}\left(\begin{array}{c}R^{17}\\-N-CH_2-N\end{array}\diagdown\begin{array}{c}CO-N-R^{11}\\|\\CO-N-R^{12}\end{array}\right)_o \quad (VIII)$$
$$R^{12}-N-CO\diagup\quad\quad R^{17}$$

in which
R$^{11}$ and R$^{12}$ have the abovementioned meaning,
R$^{17}$ represents hydrogen, C$_1$–C$_4$-alkyl, cyclohexyl, benzyl, phenyl, a heterocyclic radical or $$-CH_2-N\diagdown\begin{array}{c}CO-N-R^{11}\\|\\CO-N-R^{12}\end{array}$$

R$^{18}$ represents a (o+1) valent aliphatic radical, cyclohexane radical, benzene radical or heterocyclic radical and
o denotes the number 1 to 2, it also being possible for R$^{18}$ to be the carbonyl group if o=1,
are also preferred.

Furthermore, a process has been found for the preparation of triazolidine-3,5-dione/formaldehyde/amine condensates of the formula (I)

$$R^5-N\diagdown\begin{array}{c}CO-N-R^1\\|\\CO-N-R^2\end{array}\quad (I)$$

in which
R$^1$ and R$^2$ independently of one another represent hydrogen, alkylcarbonyl or $$-CH_2-N\diagdown\begin{array}{c}R^3\\R^4\end{array}$$

wherein
R$^3$ denotes hydrogen, alkyl, cycloalkyl, aralkyl, aryl or a heterocyclic radical and
R$^4$ denotes alkyl, alkenyl, aralkyl, aryl, a heterocyclic radical, alkylcarbonyl, alkenylcarbonyl or alkoxycarbonyl,
or wherein
R$^3$ and R$^4$, together with the nitrogen atom of which they are substituents, can denote a nitrogen-heterocyclic radical which optionally contains other hetero-atoms, and
R$^5$ represents alkyl, cycloalkyl, aralkyl, aryl, alkylcarbonyl of the group $$-CH_2-N\diagdown\begin{array}{c}R^3\\R^4\end{array},$$

in which
R$^3$ and R$^4$ have the meaning given, or
R$^5$ represents the group $$-R^6\left(-N\diagdown\begin{array}{c}CO-N-R^1\\|\\CO-N-R^2\end{array}\right)_n,$$

in which
R$^6$ represents a (n+1)-valent aliphatic, cycloaliphatic, araliphatic or aromatic radical,
R$^1$ and R$^2$ have the meaning given and n denotes the number 1 or 2, or
R$^5$ represents the group $$-CH_2-N-R^8\left(\begin{array}{c}R^7\\|\\-N-CH_2-N\end{array}\diagdown\begin{array}{c}CO-N-R^1\\|\\CO-N-R^2\end{array}\right)_n,$$
$$\quad\quad R^7$$

in which
R$^7$ denotes hydrogen, alkyl, cycloalkyl, aralkyl, aryl, a heterocyclic radical or $$-CH_2-N\diagdown\begin{array}{c}CO-N-R^1\\|\\CO-N-R^2\end{array}$$

R$^8$ denotes a (m+1)-valent aliphatic, cycloaliphatic, araliphatic, aromatic or heterocyclic radical,
R$^1$ and R$^2$ have the meaning given and
m denotes the number 0, 1 to 2, a hydrogen atom occurring instead of the radical in brackets if m=0 and it being possible for R$^8$ additionally to be a carbonyl group if m=1,
the formula given containing at least one group $$>N-CH_2-N<$$

arising from formaldehyde/amine condensation. which is characterised in that triazolidine-3,5-diones of the formula $$R^{33}-N\diagdown\begin{array}{c}CO-N-R^{31}\\|\\CO-N-R^{32}\end{array}\quad (IX)$$

in which $R^{31}$ and $R^{32}$ independently of one another denote hydrogen or alkylcarbonyl and $R^{33}$ denotes hydrogen, alkyl, cycloalkyl, aralkyl, aryl, alkylcarbonyl or the group

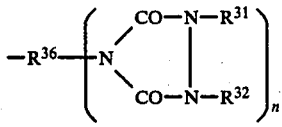

in which $R^{36}$ represents a (n+1)-valent aliphatic, cycloaliphatic, araliphatic or aromatic radical radical and n denotes the number 1 or 2, at least one of the radicals $R^{31}$, $R^{32}$ and $R^{33}$ denoting hydrogen, are reacted with formaldehyde and nitrogen compounds of the formula (X)

$$H-X \qquad (X)$$

in which

X represents

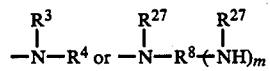

wherein $R^3$, $R^4$, $R^8$ and m have the meaning given and $R^{27}$ denotes hydrogen, alkyl, cycloalkyl, aralkyl, aryl or a heterocyclic radical, at temperatures from 10° to 180° C., if desired in the presence of a catalyst and if desired in the presence of a solvent.

The scope of meaning of the substituents in the formulae given corresponds to the scope of meaning disclosed above.

The triazolidine-3,5-diones of the formula (IX) to be employed according to the invention can be prepared by various processes.

Thus, one can to react amines of the formula (XV)

$$R^{33}(NH_2)_{n+1} \qquad (XV)$$

wherein $R^{33}$ and n have the meaning given in the case of formula (IX), with hydrazodicarboxamide (process 1) or with 1,2,4-triazolidine-3,5-dione (process 2) at 150°–280° C. in the presence or absence of a solvent, such as N-methyl-pyrrolidone, or of solvent mixtures under pressures from 50 mbars to 5 bars, if desired in the presence of an acid or basic catalyst, such as alcoholates or a tertiary amine, ammonia being split off, to give the starting 1,2,4-triazolidine-3,5-diones.

Another route for the preparation of the starting 1,2,4-triazolidine-3,5-diones consists of a process in which N-monosubstituted hydrazodicarboxamides of the formula (XVI)

$$[H_2N-CO-NH-NH-CO-NH-]_{n+1}R^{33} \qquad (XVI)$$

wherein $R^{33}$ and n have the meaning given in the case of formula IX, are reacted under the conditions given above for processes 1 and 2, ammonia being split off, to give the starting 1,2,4-triazolidine-3,5-diones. The N-monosubstituted hydrazodicarboxamides of the formula (XVI) can be obtained by known processes, from semicarbazide and isocyanates of the formula (XVII)

$$R^{33}(NCO)_{n+1} \qquad (XVII)$$

wherein $R^{33}$ and n have the meaning given in the case of formula (IX).

In the process according to the invention, the formaldehyde can either be passed in as a gas or metered in as an aqueous commerically available solution which contains, for example, up to 65% by weight of formaldehyde, preferably up to 40% by weight of formaldehyde, or used in the reaction mixture in polymeric form, such as in the form of trioxane or paraformaldehyde.

Nitrogen compounds of the formula (X), which have the abovementioned scope of meaning, can be employed according to the invention. Examples of nitrogen compounds of the formula (X) which may be mentioned are those of the formula

and those of the formula

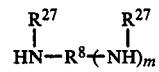

wherein the substituents have a scope of meaning within that disclosed above. Examples of nitrogen compounds of the formula (XI) which may be mentioned are: Amines, such as methylamine, ethylamine, propylamine, butylamine, hexylamine, dimethylamine, diethylamine, dipropylamine, dibutylamine, methyl-butylamine, bis-(hydroxyethyl)-amine, bis-(hydroxypropyl)-amine, cyclohexylamine, N-methyl-cyclohexylamine, aniline, N-methyl-aniline, piperidine, piperazine, morpholine and thiomorpholine, pyrrolidine, indole, carbazole, pyrazole, 2-methyl-imidazole, benzimidazole and 1,2,4-triazole. Secondary amines are preferably employed;

Amides, such as acetamide, propionamide, butyramide, 2-pyrrolidone, ε-caprolactam, 2-chloropropionamide, valeramide, stearamide, benzamide, acetanilide, acrylamide and methacrylamide.

Cyclic amides, such as ε-caprolactam, parabanic acid, bis-parabanic acids of the general formula

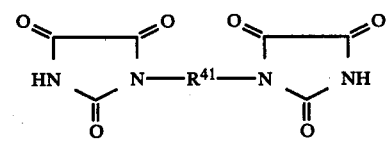

in which $R^{41}$ represents $C_2$–$C_{10}$-alkylene, $C_4$–$C_{10}$-cyclo-alkylene or $C_6$–$C_{14}$-arylene, preferably $C_2$–$C_4$-alkylene, cyclohexylene or phenylene, and hydantoins of the general formula

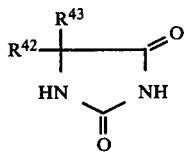

(XIV)

in which
R$^{42}$ and R$^{43}$ represent alkyl, cycloalkyl or aryl,
or wherein
R$^{42}$ and R$^{43}$ together can form a trimethylene, tetramethylene, pentamethylene, hexamethylene or heptamethylene group.

Further cyclic amides which may be mentioned are bis-hydantoins, which can be linked via the 1,1-position or 3,3-position, barbituric acid and cyclic imides, such as succinimide or phthalimide.

Examples of nitrogen compounds of the formula (XII) which may be mentioned are aliphatic, cycloaliphatic, araliphatic, aromatic or heterocyclic polyamines, such as ethylenediamine, trimethylenediamine, tetramethylenediamine, diamines of the type mentioned which are alkyl-substituted on the nitrogen atom, phenylenediamine, melamine, 4,6-diamino-2-phenyl-1,3,5-triazine, 1,2-bis-(4,6-diamino-1,3,5-triazin-2-yl)-ethane, 1,4-bis-(4,6-diamino-1,3,5-triazin-2-yl)-butane and 1,6-bis- and 1,3,6-tris-(4,6-diamino-1,3,5-triazin-2-yl)-hexane.

The process according to the invention is carried out at a temperature from 10° to 180° C., preferably 20° to 160° C. The reaction of the process according to the invention frequently proceeds as an exothermic reaction, especially if a suitable catalyst is used, so that it is expedient to start the reaction at a lower temperature, within the range mentioned, and to bring the reaction to completion, with or without cooling, at a higher temperature within the range mentioned. In the case where the reaction is carried out as a multi-stage reaction, as described below, it may be necessary for the first stage to be carried out at a lower temeprature within the range mentioned and for the second stage to be carried out at a higher temperature within the range mentioned.

If low-boiling reactants are used, and in order to avoid formaldehyde losses, it may be necessary to carry out the reaction under increased pressure. A range from 1 to 8, preferably 1 to 5, bars may be mentioned as an example of increased pressure.

The process according to the invention can be carried out without or with solvents. The absence of solvents is possible if the reaction is carried out in a melt of the reactants or if one reactant, for example the nitrogen compound, is liquid and the other reactant dissolves completely or partly.

In the case where the reaction is carried out in the presence of a solvent, polar solvents which do not react with the reactants may be mentioned as the solvent. Examples of these are: ethers, such as dibutyl ether, ethylene glycol dimethyl ether, dioxane or tetrahydrofuran, esters, such as butyl acetate or glycol monomethyl ether-acetate, N,N-dialkylated amides, such as dimethyl-formamide, dimethylacetamide or N-methylpyrrolidone, sulphones, such as dimethyl sulphone or tetramethylene sulphone, as well as water and mixtures of water and those water-miscible solvents from the list of examples. When the reaction has ended, further solvents, such as, for example, aliphatic or aromatic hydrocarbons, such as ligroin, cyclohexane, toluene or xylene, chlorinated hydrocarbons, such as methylene chloride, chloroform or chlorobenzene, alcohols, such as ethanol or butanol, or ketones, such as acetone or butanone, can be added if appropriate, for example for better working up of the reaction mixture, for example by crystallisation or extraction. In many cases, water can be used as the solvent since the desired compound thereby crystallises out or can be crystallised by adding precipitating agents, such as ethanol or acetone. In such cases, the formaldehyde can advantageously be employed as aqueous formalin solution. This process variant is thus preferred.

In the case where the reaction is carried out in the presence of a solvent, an amount of 25 to 1,000% by weight, preferably 100 to 600% by weight, of solvent, relative to the total amount of reactants, may be mentioned.

The process according to the invention can be carried out either as a one-stage process or in two stages. In the one-stage process, for example, the triazolidine-3,5-dione and the nitrogen compound, if appropriate in one of the solvents mentioned, can be initially introduced into the reaction vessel. The formaldehyde is then metered in. In a preferred embodiment, aqueous formaldehyde is used. An exothermic reaction is first observed, and the reaction is then brought to completion by warming to the desired reaction temperature. Proportions of triazolidine-3,5-dione, nitrogen compound and formaldehyde which may be mentioned are, for example in the case where each NH group present in the triazolidinedione is to be reacted, 0.8 to 3 mols, preferably 0.8 to 1.5 mols and particularly preferably 0.9 to 1.1 mols, each of formaldehyde and nitrogen compound per NH group equivalent. However, if one or two NH groups are not to be reacted, the excess of formaldehyde and nitrogen compound must be limited, and 0.9 to 1.1 mols each of formaldehyde and nitrogen compound per NH group equivalent may be mentioned as an example of the amount in this case.

The reaction product can be worked up and purified by customary methods, for example by crystallisation.

In the two-stage procedure, the process according to the invention can be carried out by two variants. In the first variant, the corresponding methylol compound is first formed from the triazolidine-3,5-dione and formaldehyde, and this methylol compound is then reacted further with the nitrogen compound. However, as a second variant, it is also possible first to form the associated methylol compound from the nitrogen compound and formaldehyde and then subsequently to further react the methylol compound with the triazolidine-3,5-dione.

The individual part steps described for the process according to the invention and the one-stage variant of the process according to the invention can be carried out either with or without the use of catalysts. The use of catalysts generally lowers the reaction temperature and generally shortens the reaction times, so that it is preferable to use a suitable catalyst.

Basic catalysts, for example, can be used for the reaction of the triazolidine-3,5-diones with formaldehyde which is possible as the first part step. Examples of such catalysts which may be mentioned are: tertiary amines or quaternary ammonium salts, such as triethylamine, tri-n-butylamine, triethanolamine, N,N-dimethylaniline or tetramethylammonium chloride, alkali metal hydroxides and alkaline earth metal hydroxides, such as sodium hydroxide, potassium hydroxide or barium hyroxide, basic alkali metal salts or alkaline earth metal salts, such as sodium tetraborate, sodium aluminate, lithium carbonate, sodium carbonate, potassium carbonate or barium carbonate, or alcoholates, such as sodium methylate. An amount of catalyst of 0.001 to 5% by weight, preferably 0.05 to 2% by weight, relative to the total weight of the reactants, may be mentioned as an example.

However, in the case where the formaldehyde is employed in polymeric form, such as in the form of trioxane or paraformaldehyde, acid catalysts are also suitable. Examples of acid catalysts which may be mentioned are: mineral acids, such as hydrochloric acid, phosphoric acid or sulphuric acid, sulphonic acids, such as p-toluenesulphonic acid, or organic acids, such as oxalic acid, acetic acid, formic acid or benzoic acid.

In the case where the reaction of the nitrogen compound with formaldehyde is carried out as the first stage of a two-stage process variant, this reaction can likewise be carried out in the presence of a basic catalyst. The basic catalysts and the amount thereof described above can be employed for this process variant.

In the first stage of a two-stage process variant, the formaldehyde reacts with a hydrogen bonded to a nitrogen atom in the triazolidine-3,5-dione or in the nitrogen compound, to form a methylol group. In this reaction, formaldehyde is employed in an amount of 0.8 to 1.5, preferably 0.9 to 1.1, mols per equivalent of the hydrogen which is located on a nitrogen atom and is to be reacted. Other N—H groups which may be present and for the reaction of which there is no formaldehyde present in the reaction mixture are retained as such. If all the N—H groups present are to be converted into methylol groups, an excess of formaldehyde greater than the abovementioned amount of formaldehyde is possible. The excess, for example 0.1 to 2 mols greater than the abovementioned amount, can accelerate the reaction in the first stage of a two-stage process variant. However, it must largely be removed again before the second stage in order to avoid interfering side reactions.

If, in the second stage of a two-stage process variant, the nitrogen compound is added to the triazolidine-3,5-dione-methylol compound which has already been formed, or if, in the second stage of a two-stage process variant, the triazolidine-3,5-dione is added to the methylol compound which has already been formed from the nitrogen compound, it is possible to use a basic or acid catalyst such as has already been described above. Thus, if the first stage of such a two-stage process variant is carried out using a catalyst, it is as a rule not necessary to add an additional catayst in the second reaction stage. The amount of nitrogen compound added in the second stage to the triazolidine-3,5-dione methylol compound which has already been formed, or the amount of triazolidine-3,5-dione added to the methylol compound which has already been formed from the nitrogen compound is, for example, 0.8 to 1.5 mols, preferably 0.9 to 1.1 mols, relative to each methylol group which has already been formed. In the case where the nitrogen compound is added, in the second stage, to the triazolidine-3,5-dione-methylol compound which has already been formed, it is also possible to use more than the abovementioned amount, for example 0.1 to 2 mols more than the abovementioned amount. Such an excess of nitrogen compound can serve, for example, as a solvent or an an additional solvent. The use of such an excess and its amount generally depend on the requirements in respect of ease of working up of the reaction mixture.

In the two-stage process variant of the process according to the invention, that variant in which the triazolidine-3,5-dione-methylol compound is first formed and the nitrogen compound is added in a second stage is preferred. In this variant, the first reaction stage is carried out in the lower part of the temperature range described above, for example at room temperature, and the second stage is carried out in the upper part of the temperature range, for example at 50 to 180° C., preferably at 80 to 160° C.

The triazolidine-3,5-dione/formaldehyde/amine condensates according to the invention are valuable auxiliaries for modifying polymeric substances. They can thus be employed, for example, for the preparation and for the modification of melamine resins, urea resins and phenolic resins. The substances according to the invention are suitable for this purpose either in the form of individual compounds or as mixture of substances with a different degree of methylolation and a different degree of condensation. Thus resols, for example, produced from phenol and formaldehyde, can be mixed with the triazolidine-3,5-dione/formaldehyde/amine condensates according to the invention and, optionally after adding additives such as for example sawdust and optionally after adding, preferably, acid catalysts, such as for example phosphoric acid, can be processed into laminates by heating such mixtures under pressure. The quantity of triazolidine-3,5-dione/formaldehyde/amine condensates can vary within wide limits and is usually between 2 and 80% by weight, preferably between 5 and 50% by weight, based on the quantity of polymer. The triazolidine-3,5-dione/formaldehyde/amine condensates according to the invention can also be employed as flameproofing agents, for example in thermoplastic polyamide moulding compositions. A triazolidine-3,5-dione/formaldehyde/amine condensate of the invention is for flame proofing purposes included in such thermoplastic polyamide composition in an amount of between 0.1 and 20 weight percent, preferably between 2 and 15 weight percent.

EXAMPLES

Unless indicated otherwise, percentages denote percentages by weight and parts denote parts by weight.

Example 1

(a) Preparation of

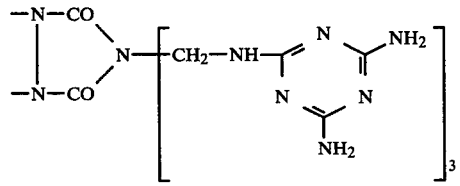

3.03 kg of triazolidine-3,5-dione are added to 9,75 kg of 37% strength aqueous formaldehyde solution, which contains 10 g of borax, whilst stirring, and the mixture is warmed to 100° C. The resulting clear solution is stirred at 100° C. for 90 minutes and concentrated by distilling off the water under a waterpump vacuum, the excess formaldehyde also being removed. The cooled light-yellow viscous liquid, which is chiefly trishydroxymethyl-triazolidine-3,5-dione, is dissolved in 90 l of deionised water at room temperature, 11.34 kg of melamine are added and the mixture is warmed slowly until the water refluxes. The resulting mixture is stirred under reflux for two hours and filtered at 90° C. and the residue is washed with hot water. After drying the material on the filter at 100° C. and under 30 mbars, 14.55 kg of product of the above formula, which is confirmed by means of the IR spectrum and elementary analysis, are obtained.

Calculated for $C_{14}H_{21}N_{21}O_2$: C=32.7% H=4.08%, N=57.1%; found: C=32.9%, H=4.2%, N=56.5%.

Melting point >260° C.

(b) 85% by weight of polyamide-6,6 with a relative viscosity (measured on a solution of 1 g of polyamide in 100 ml of m-cresol at 25° C.) of 2.96 are mixed, in the melt in a twin-screw extruder under the conditions customary for polyamide-6,6, with 15% by weight of the Mannich condensate prepared according to (a). The extruded strand is cooled and granulated and the granules are dried. The granules are then injection-moulded in a A 270 injection-moulding machine from Messrs. Arburg to give test pieces with the dimensions 127×12.7×1.6 mm.

These test pieces are kept at 23° C. and at 50% relative atmospheric humidity for 24 hours and, when subjected to the burning test in which the after-burn times are to be determined from 10 flamings, have an after-burn time of 11 seconds, whilst test pieces containing no Mannich condensate have an after-burn time of 32 seconds.

Example 2

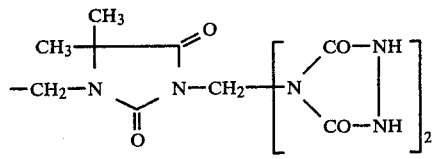

163 g of 37% strength formaldehyde solution containing 2 g of borax are warmed to 80° C. with 128 g of 5,5-dimethyl-hydantoin, and the mixture is stirred at 80° C. for 2 hours. The resulting clear solution is cooled and, after adding 202 g of triazolidine-3,5-dione, the mixture is stirred under reflux for 3 hours. The concentrated solution is dissolved in a little ethanol and freed from a small amount of insoluble residue. The ethanolic solution is freed from the solvent and from residual water by heating to 160° C. 335 g of a brittle material which has a resinous appearance and predominantly consists of the substance of the above formula, the structure of the substance being proved by means of the IR spectrum and NMR spectrum and by elementary analysis, are obtained.

Calculated for $C_{11}H_{14}N_8O_6$: C=37.3%, H=3.95%, N=31.6%; found: C=37.0%, H=3.8%, N=31.2%.

Example 3

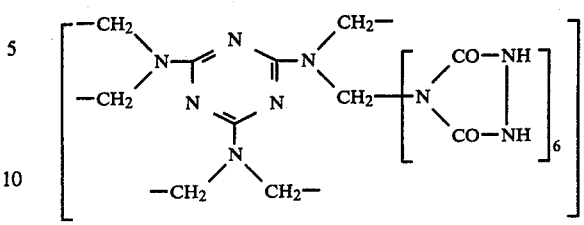

30.6 g of hexamethylolmelamine, prepared in accordance with the method of Sorensen and Campbell, Präparative Methoden der Polymeren Chemie (Preparative Methods of Polymeric Chemistry), Verlag Chemie 1962, and 60.6 g of triazolidine-3,5-dione in 500 ml of water are warmed to 95° C., and the mixture is stirred at 95° C. for 2.5 hours. After cooling the mixture to room temperature, the precipitate is filtered off and washed with water. 61 g of dried product which predominantly consists of the substance of the above formula, the structure of the substance being proved by means of the IR spectrum and NMR spectrum and by elementary analysis, are obtained.

Calculated for $C_{21}H_{24}N_{24}O_{12}$: C=31.3%, H=2.99%, N=41.7%; found: C=31.1%, H=3.2%, N=41.6%.

Example 4

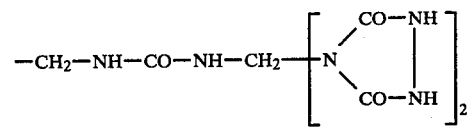

60 g of dimethylolurea are dissolved in 100 ml of water, the pH is adjusted to 8 with 10% strength sodium hydroxide solution, 101 g of triazolidine-3,5-dione are added and the mixture is stirred at 100° C. for 3 hours. The product is precipitated from the cooled solution by adding ethanol and the precipitate is filtered off, washed with ethanol and methanol and dried. 125 g of product which predominantly consists of the substance of the above formula, the structure of the substance being proved by means of the IR spectrum and NMR spectrum and by elementary analysis, are thus obtained.

Calculated for $C_7H_{10}N_8O_5$: C=29.4%, H=3.5%, N=39.2%; found: C=29.2%, H=3.8%, N=39.0%.

Example 5

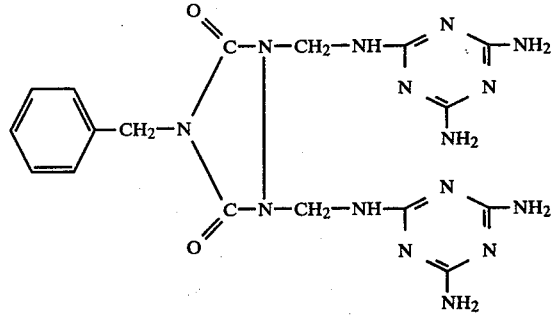

38.2 g of 4-benzyl-triazolidine-3,5-dione are added to 32.8 g of 37% strength aqueous formaldehyde solution, which contained 0.1 ml of 45% strength sodium hydroxide solution, at room temperature and the mixture is stirred at 50° C. for one hour. The clear solution is diluted with 500 ml of water, 50.4 g of melamine are added and the mixture is heated to 95° C. and stirred at 95° C. for 3 hours in order to bring the reaction to completion. The resulting precipitate is filtered off hot, washed with water and dried at 100° C./40 mbars. 92 g of product of the above formula, which is proved by means of the IR spectrum and by elementary analysis, are obtained.

Calculated for $C_{17}H_{21}N_{15}$: C=45.7%, H=4.5%, N=45%; found: C=45.3%, H=4.3%, N=45.4%.

Example 6

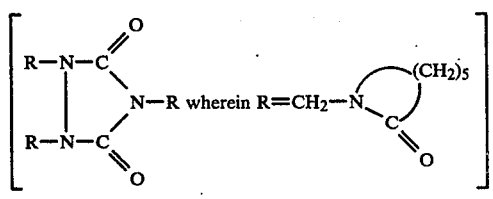

20.2 g of triazolidine-3,5-dione are added in portions to 45 g of aqueous 37% strength formaldehyde solution at temperatures <50° C., and the mixture is stirred at 50° C. for one hour. The resulting clear solution is concentrated by applying a vacuum, and 67.8 g of ε-caprolactam, 250 ml of toluene and 0.5 g of p-toluenesulphonic acid are added to the colourless viscous residue. The resulting mixture is heated to the reflux temperature for 8 hours, during which the last residues of water and the water formed during the condensation are continuously removed by means of a water separator. After cooling to room temperature, the toluene solution is decanted from a small amount of residue and is rinsed with 100 ml of water. After drying over sodium sulphate, the organic phase is concentrated in a rotary evaporator and the residue is dried to constant weight under 0.5 mbar and at 60° C. 62.4 g of a compound which is almost pure according to thin layer chromatography remain in the form of a colourless oil which starts to crystallise after some hours, the structure of the oil being confirmed by means of the IR spectrum and NMR spectrum and by elementary analysis.

Calculated for $C_{23}H_{36}N_6O_5$: C=57.9%, H=7.56%, N=17.6%; found: C=57.6%, H=7.5%, N=17.5%.

Example 7

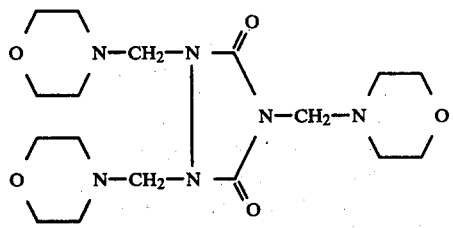

20.2 g of triazolidine-3,5-dione are added to 44.8 g of 37% strength aqueous formaldehyde solution, which contained 0.1 ml of 45% strength sodium hydroxide solution, at room temperature and the mixture is stirred at 50° C. for one hour. The clear solution is concentrated by applying a vacuum, 80 g of morpholine, 250 ml of toluene and 0.5 g of p-toluenesulphonic acid are added and the mixture is stirred under reflux for 8 hours, the residual water and the water formed during the reaction being removed via a water separator. The cold toluene solution is rinsed with water and, after drying over $Na_2SO_4$, concentrated in a rotary evaporator. The oily residue which remains crystallises completely after some hours and, after adding a little cyclohexane, the crystals can be filtered off. 36 g of a colourless crystalline compound which, after recrystallisation from cyclohexane, has a melting point of 118°–119° C. and which has the above formula, which is confirmed by the IR spectrum and NMR spectrum and by elementary analysis, are obtained.

Calculated for $C_{17}H_{30}N_6O_5$: C=51.2%, H=7.54%, N=21.1%; found: C=51.4%, H=7.4%, N=21.1%.

EXAMPLE 8

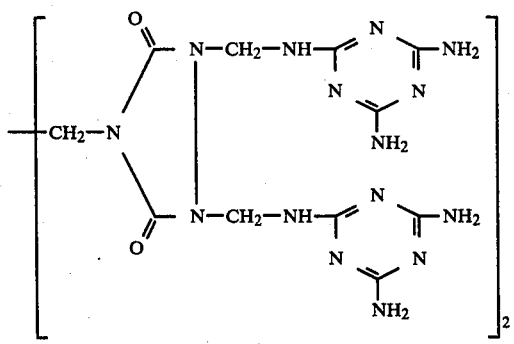

22.8 g of 1,2-ethanediyl-4,4'-bis-1,2,4-triazolidine-3,5-dione are added to 33 g of 37% strength aqueous formaldehyde solution, which contained 0.1 ml of 45% strength sodium hydroxide solution, at room temperature and, when the slightly exothermic reaction has ended, the mixture is stirred at 50° C. for one hour. The clear solution is diluted with 500 ml of water, 50.4 g of melamine are added and the mixture is heated to 95° C. and stirred at 95° C. for 2 hours. The resulting precipitate is filtered off hot, washed with water and dried at 100° C./35 mbars. 76.2 g of product which has a melting point >260° C. and the above formula, which is proved by means of the IR spectrum and by elementary analysis, are obtained.

Calculated for $C_{22}H_{16}N_{30}O_4$: C=33.8%; H=4.12%; N=54.8%; found: C=34.1%; H=4.3%; N=54.5%.

In flameproofing tests on thermoplastic polyamide-6,6, similar results to those in Example 1b are achieved with this compound.

EXAMPLE 9

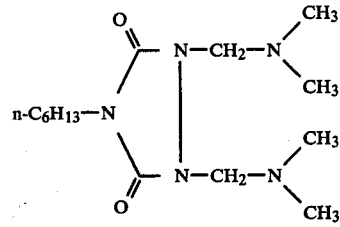

37 g of 4-(n-hexyl)-triazolidine-3,5-dione are added to 33 g of 37% strength aqueous formaldehyde solution, which contained 0.1 g of sodium carbonate, at room temperature. When the exothermic reaction has ended, 40 g of 52% strength aqueous dimethylamine solution are added dropwise and the mixture is stirred at 80° C. for 2 hours. After distilling off the water, the mixture was filtered over silica gel and the volatile constituents were removed, the final temperature being 50° C. and the final pressure being 0.3 mbar. 29.1 g of a brown oil, the IR and NMR spectra and elementary analysis of which confirm the above formula, are obtained.

Calculated for $C_{14}H_{29}N_5O_2$: C=56.2%; H=9.81%; N=23.4%; found: C=55.8%; H=9.5%; N=23.7%.

EXAMPLE 10

3 kg of sulpholane and 1.18 kg of hydrazodicarboxamide, which has been dried in air, are heated to 200° C. in a 6-l three-necked flask, which is provided with a stirrer, thermometer, dropping funnel and distillation device, in the course of 2.5 hours, a slight vacuum being applied at the start of the evolution of ammonia at 150°-160° C. The temperature is then increased to 210° C. in the course of one hour. After about 1.5 hours, a clear solution is formed, and stirring is continued at 210° C. and under 200 mbars for about a further 3.5 hours, until the reaction has ended. After cooling the mixture to 180° C., the residual ammonia is removed under 40 to 80 mbars. 0.8 kg of toluene are added dropwise to the cooling solution under normal pressure is a manner such that virtually no toluene is distilled off. After cooling the mixture to room temperature, the almost pure 1,2,4-triazolidine-3,5-dione which has crystallised out is filtered off and washed with toluene. 0.87 kg (=86.2% of the theoretical yield) of dried 1,2,4-triazoline-3,5-dione with a purity of 97.5%, determined by titration with N/10 sodium hydroxide solution using phenol phthalein, is obtained.

EXAMPLE 11

53.5 g of benzylamine and 59 g of hydrazodicarboxamide in 100 ml of N-methylpyrrolidone are stirred at 175° C. for 4 hours and at 200° C. for 5 hours. The solvent is then distilled off in vacuo, the residue is triturated with 50 ml of 10% strength sodium hydroxide solution, and the resulting residue is filtered off. The filtrate is neutralised with 10% strength hydrochloric acid. A precipitate is thereby formed and is filtered off and washed with water. 67 g (70% of the theoretical yield) of 4-benzyl-1,2,4-triazolidine-3,5-dione are obtained as colourless cyrstals of melting point 185°-188° C. ($CH_3CN$).

EXAMPLE 12

600 g of hydrazodicarboxamide and 150 g of ethylenediamine in 500 ml of N-methylpyrrolidone are stirred at 175° C. for 4 hours and at 200° C. for 20 hours. On cooling, a precipitate separates out, and is filtered off and washed with ethanol. 462 g (80% of the theoretical yield) of 1,2-ethanediyl-4,4'-bis-1,2,4-triazolidine-3,5-dione are obtained as colourless crystals of melting point >330° C.

EXAMPLE 13

60 g of hydrazodicarboxamide and 56 g of n-hexylamine in 100 ml of N-methylpyrrolidone are stirred at 150° C. for 6 hours, at 175° C. for 20 hours and at 180° C. for 20 hours. The solvent is then distilled off in vacuo and the residue is triturated with 100 ml of 10% strength sodium hyroxide solution. The precipitate is filtered off and the filtrate is neutralised with 10% strength hydrochloric acid. A precipitate thereby separates out, and is filtered off, washed with water and dried in vacuo. 75 g (81% of the theoretical yield) of 4-(n-hexyl)-1,2,4-triazolidine-3,5-dione are obtained as colourless crystals of melting point 144°-145° C.

What is claimed is:

1. A compound of the formula

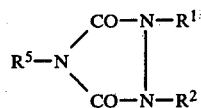

wherein $R^1$ and $R^2$, independently of one another are each hydrogen, alkylcarbonyl having 2 to 21 carbon atoms or

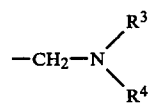

wherein $R^3$ is hydrogen, alkyl having 1 to 20 carbon atoms, cycloalkyl having 3 to 10 carbon atoms, unsubstituted aralkyl having up to 14 carbon atoms in the aryl moiety and up to 2 carbon atoms in the alkyl moiety, unsubstituted aryl having 6 to 14 carbon atoms, or a heterocyclic radical selected from the group consisting of a radical of pyrrolidine, piperidine, pyrazolidine, imidazolidine, oxazolidine, thiazolidine, piperazine, morpholine, thiomorpholine, hydantoin, 5,5-dimethylhydantoin, parabanic acid, barbituric acid and cyanuric acid and $R^4$ is alkyl having 1 to 20 carbon atoms, alkenyl having 2 to 20 carbon atoms, unsubstituted aralkyl having up to 14 carbon atoms in the aryl moiety and up to 2 carbon atoms in the alkyl moiety, unsubstituted aryl having 6 to 14 carbon atoms, or a heterocyclic radical selected from the group consisting of a radical of pyrrolidine, piperidine, pyrazolidine, imidazolidine, oxazolidine, thiazolidine, piperazine, morpholine, thiomorpholine, hydantoin, 5,5-dimethylhydantoin, parabanic acid, barbituric acid and cyanuric acid, alkylcarbonyl having 2 to 21 carbon atoms, alkenylcarbonyl having 3 to 21 carbon atoms or alkoxycarbonyl having 2 to 20 carbon atoms, or wherein $R^3$ and $R^4$, together with the nitrogen atom to which they are attached, form a nitrogen-containing heterocyclic radical selected from the group consisting of a radical of pyrrolidine, pyrazolidine, imidazolidine, oxazolidine, thiazolidine, triazolidine, tetrazolidine, thiodiazolidine, piperidine, piperazine, morpholine, thiomorpholine, azacyclobutane and azacycloheptane, and $R^5$ is alkyl having 1 to 20 carbon atoms, cycloalkyl having 3 to 10 carbon atoms, unsubstituted aralkyl having up to 14 carbon atoms in the aryl moiety and up to 2 carbon atoms in the alkyl moiety, unsubstituted aryl having 6 to 14 carbon atoms, alkylcarbonyl having 2 to 21 carbon atoms or

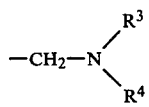

wherein
R³ and R⁴ are as aforesaid or
R⁵ is of the formula

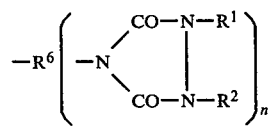

wherein
R⁶ is a (n+1)-valent $C_1$–$C_{20}$ aliphatic, $C_3$–$C_{10}$ cycloaliphatic, $C_8$–$C_{16}$ araliphatic or $C_6$–$C_{14}$ aromatic hydrocarbon radical or one of said hydrocarbon radicals mono- or di-substituted by halogen, hydroxyl, $C_1$–$C_4$-alkoxy, cyano, amino, $C_1$–$C_4$-alkylamino, bis-($C_1$–$C_4$-alkyl)-amino, $C_2$–$C_4$-alkoxycarbonyl or $C_1$–$C_4$-alkyl,
R¹ and R² are as aforesaid and
n is 1 or 2 or
R⁵ is of the formula

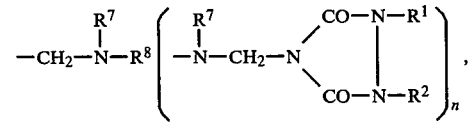

wherein
R⁷ is hydrogen, alkyl having 1 to 20 carbon atoms, cycloalkyl having 3 to 10 carbon atoms, unsubstituted aralkyl having up to 14 carbon atoms in the aryl moiety and up to 2 carbon atoms in the alkyl moiety, unsubstituted aryl having 6 to 14 carbon atoms, a heterocyclic radical selected from the group consisting of a radical of pyrrolidine, piperidine, pyrazolidine, imadazolidine, oxazolidine, thiazolidine, piperazine, morpholine, thiomorpholine, hydantoin, 5,5-dimethylhydantoin, parabanic acid, barbituric acid and cyanuric acid or

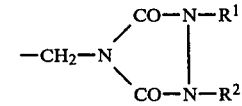

R⁸ is a (m+1)-valent $C_1$–$C_{20}$-aliphatic, $C_3$–$C_{10}$-cycloaliphatic, $C_8$–$C_{16}$-araliphatic, $C_6$–$C_{14}$-aromatic hydrocarbon radical or one of said hydrocarbon radicals mono- or di-substituted by halogen, hydroxyl, $C_1$–$C_4$-alkoxy, cyano, amino, $C_1$–$C_4$-alkylamino, bis-($C_1$–$C_4$-alkyl)-amino, $C_2$–$C_4$-alkoxycarbonyl or $C_1$–$C_4$-alkyl,
R¹ and R² are as aforesaid and
m is 0, 1 and 2, a hydrogen atom being present instead of the radical in brackets if m is 0 and it being possible for R⁸ to be a carbonyl group when m is 1, said R¹, R² and R⁵ being selected so that said compound of said formula contains at least one group of the formula

2. A compound according to claim 1 of the formula

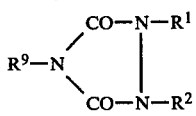

wherein R⁹ is alkyl having 1 to 20 carbon atoms, cycloalkyl having 3 to 10 carbon atoms, unsubstituted aralkyl having up to 14 carbon atoms in the aryl moiety and up to 2 carbon atoms in the alkyl moiety, unsubstituted aryl having 6 to 14 carbon atoms, alkylcarbonyl having 2 to 21 carbon atoms or

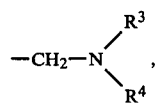

said R¹, R² and R⁹ being selected so that said compound contains at least one group of the formula

3. A compound according to claim 1 of the formula

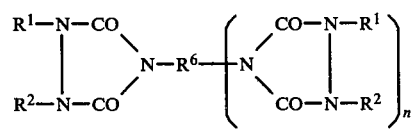

4. A compound according to claim 1 of the formula

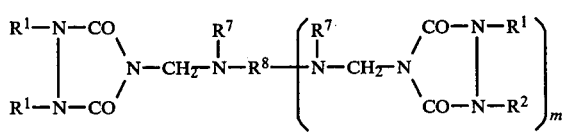

5. A compound according to claim 1 of the formula

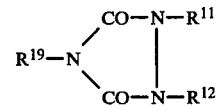

in which
R¹¹ and R¹² independently of one another denote hydrogen, $C_2$–$C_8$-alkylcarbonyl or

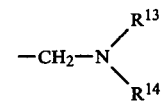

wherein
R¹³ represents hydrogen, $C_1$–$C_8$-alkyl, $C_5$–$C_6$-cycloalkyl, benzyl or phenyl and
R¹⁴ denotes $C_1$–$C_8$-alkyl, $C_2$–$C_8$-alkenyl, benzyl, phenyl a heterocyclic radical selected from the group consisting of a radical of pyrrolidine, piperidine, pyrazolidine, imidazolidine, oxazolidine, thiazolidine, piperazine, morpholine, thiomorpholine, hydantoin, 5,5-dimethylhydantoin, parabanic acid, barbituric acid and cyanuric acid, $C_2$-$C_8$-alkylcarbonyl, $C_3$-$C_8$-alkenylcarbonyl or $C_2$-$C_8$-alkoxycarbonyl, and in which
$R^{13}$ and $R^{14}$, together with the nitrogen atom to which they are attached, form a nitrogen-containing heterocyclic radical selected from the group consisting of a radical of pyrrolidine, pyrazolidine, imidazolidine, oxazolidine, thiazolidine, triazolidine, tetrazolidine, thiodiazolidine, piperidine, piperazine, morpholine, thiomorpholine, azacyclobutane and azacycloheptane, and $R^{19}$ represents $C_1$-$C_8$-alkyl, $C_5$-$C_6$-cycloalkyl, benzyl, phenyl, $C_2$-$C_8$-alkylcarbonyl or

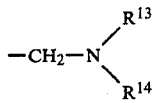

wherein
$R^{13}$ and $R^{14}$ are as aforesaid, said $R^{11}$, $R^{12}$ and $R^{19}$ being selected so that said compound of said formula contains at least one group of the formula

6. A compound according to claim 1 of the formula

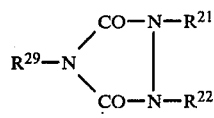

in which
$R^{21}$ and $R^{22}$ independently of one another are each hydrogen, $C_2$-$C_4$-alkylcarbonyl or

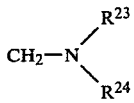

wherein
$R^{23}$ represents hydrogen or $C_1$-$C_4$-alkyl and
$R^{24}$ represents $C_1$-$C_4$-alkyl, a heterocyclic radical selected from the group consisting of a radical of pyrrolidine, piperidine, pyrazolidine, imidazolidine, oxazolidine, thiazolidine, piperazine, morpholine, thiomorpholine, hydantoin, 5,5-dimethylhydantoin, parabanic acid, barbituric acid and cyanuric acid, $C_2$-$C_4$-alkylcarbonyl or $C_3$-$C_4$-alkenylcarbonyl, and wherein
$R^{23}$ and $R^{24}$, together with the nitrogen atom to which they are attached form a nitrogen-containing heterocyclic radical selected from the group consisting of a radical of pyrrolidine, pyrazolidine, imidazolidine, oxazolidine, thiazolidine, triazolidine, tetrazolidine, thiodiazolidine, piperidine, piperazine, morpholine, thiomorpholine, azacyclobutane and azacycloheptane, and $R^{29}$ denotes $C_1$-$C_4$-alkyl, cyclohexyl, benzyl, phenyl $C_2$-$C_4$-alkylcarbonyl or

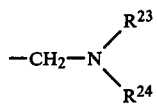

wherein
$R^{23}$ and $R^{24}$ are as aforesaid, $R^{21}$, $R^{22}$ and $R^{29}$ being selected so that said compound of said formula contains at least one group of the formula

7. A compound according to claim 1 of the formula

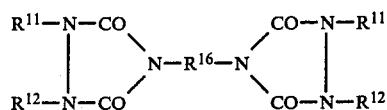

in which
$R^{11}$ and $R^{12}$ independently denote hydrogen, $C_2$-$C_8$ alkylcarbonyl or

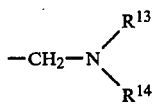

wherein
$R^{13}$ represents hydrogen, $C_1$-$C_8$ alkyl, $C_5$-$C_6$ cycloalkyl, benzyl or phenyl and
$R^{14}$ denotes $C_1$-$C_8$ alkyl, $C_2$-$C_8$ alkenyl, benzyl, phenyl a heterocyclic radical selected from the group consisting of a radical of pyrrolidine, piperidine, pyrazolidine, imidazolidine, oxazolidine, thiazolidine, piperazine, morpholine, thiomorpholine, hydantoin, 5,5-dimethylhydantoin, parabanic acid, barbituric acid and cyanuric acid, $C_2$-$C_8$-alkoxycarbonyl, $C_2$-$C_8$ alkylcarbonyl or $C_3$-$C_8$ alkenylcarbonyl, $R^{16}$ denotes alkylene, phenylene, toluylene or one of the groups

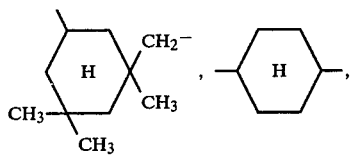

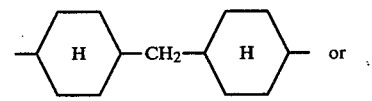

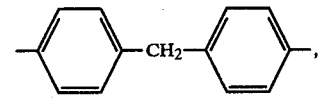

$R^{11}$, $R^{12}$ and $R^{16}$ being selected so that said compound of said formula contains at least one group of the formula

8. A compound according to claim 1 of the formula

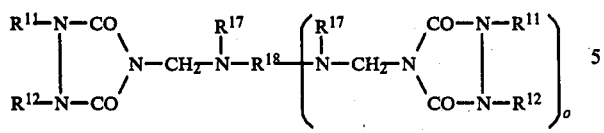

in which

R$^{11}$ and R$^{12}$ independently of one another are each hydrogen, C$_2$-C$_8$-alkylcarbonyl or

wherein

R$^{13}$ represents hydrogen, C$_1$-C$_8$-alkyl, C$_5$-C$_6$-cycloalkyl, benzyl or phenyl and R$^{14}$ denotes C$_1$-C$_8$-alkyl, C$_2$-C$_8$-alkenyl, benzyl, phenyl a heterocyclic radical selected from the group consisting of a radical of pyrrolidine, piperidine, pyrazolidine, imidazolidine, oxazolidine, thiazolidine, piperazine, morpholine, thiomorpholine, hydantoin, 5,5-dimethylhydantoin, parabanic acid, barbituric acid and cyanuric acid, C$_2$-C$_8$-alkylcarbonyl, C$_3$-C$_8$-alkenylcarbonyl or C$_2$-C$_8$-alkoxycarbonyl, and in which R$^{13}$ and R$^{14}$ together with the nitrogen atom to which they are attached form a nitrogen-containing heterocyclic radical selected from the group consisting of a radical of pyrrolidine, pyrazolidine, imidazolidine, oxazolidine, thiazolidine, triazolidine, tetrazolidine, thiodiazolidine, peperidine, piperazine, morpholine, thiomorpholine, azacyclobutane and azacycloheptane, and R$^{19}$ represents C$_1$-C$_8$-alkyl, C$_5$-C$_6$-cycloalkyl, benzyl, phenyl, C$_2$-C$_8$-alkylcarbonyl or

wherein

R$^{13}$ and R$^{14}$ are as aforesaid,

R$^{17}$ represents hydrogen, C$_1$-C$_4$-alkyl, cyclohexyl, benzyl, phenyl, a heterocyclic radical selected from the group consisting of a radical of pyrrolidine, piperidine, pyrazolidine, imidazolidine, oxazolidine, thiazolidine, piperazine, morpholine, thiomorpholine, hydantoin, 5,5-dimethylhydantoin, parabanic acid, barbituric acid and cyanuric acid or

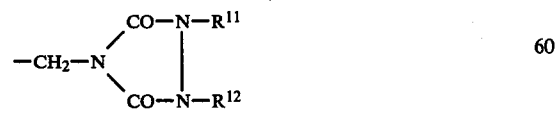

R$^{18}$ represents a (o+1)-valent aliphatic radical, cyclohexane radical, benzene radical or heterocyclic radical selected from the group consisting of a radical of pyrrolidine, piperidine, pyrazolidine, imidazolidine, oxazolidine, thiazolidine, piperazine, morpholine, thiomorpholine, hydantoin, 5,5-dimethylhydantoin, parabanic acid, barbituric acid and cyanuric acid and o denotes the number 1 or 2, it also being possible for R$^{18}$ to be the carbonyl group if o=1, R$^{11}$, R$^{12}$ and R$^{18}$ being selected so that said compound of said formula contains at least one group of the formula $>$N—CH$_2$—N$<$ 9. A compound according to claim 1 of the formula

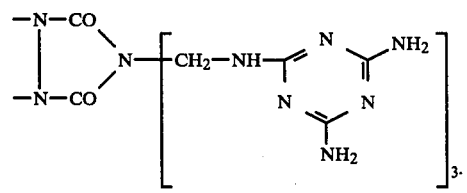

10. A compound according to claim 1 of the formula

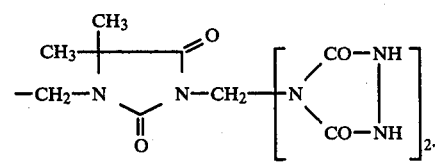

11. A compound according to claim 1 of the formula

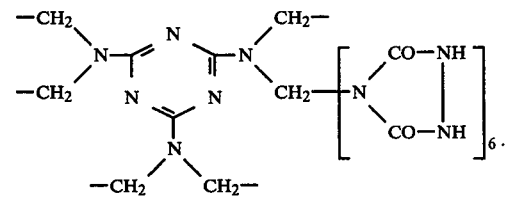

12. A compound according to claim 1 of the formula

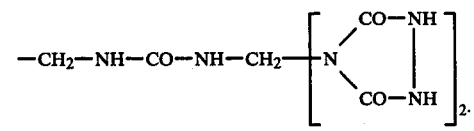

13. A compound according to claim 1 of the formula

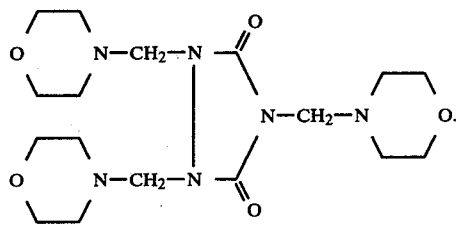
16. A compound according to claim 1 of the formula
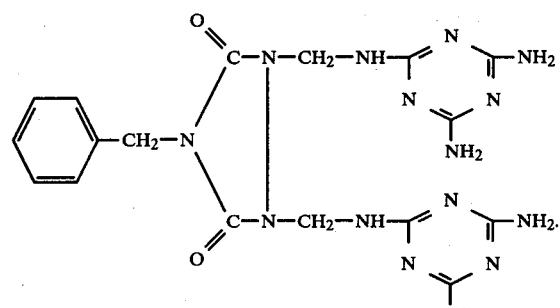
14. A compound according to claim 1 of the formula
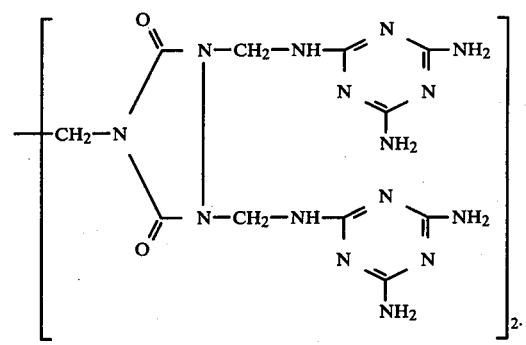
17. A compound according to claim 1 of the formula
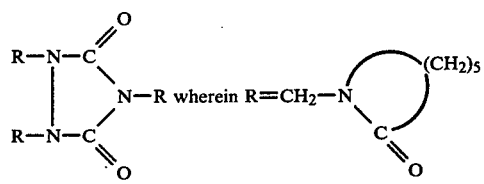
15. A compound according to claim 1 of the formula
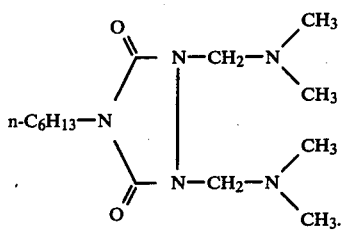
18. A polyamide molding composition containing, as a flame-proofing agent, a compound of claim 1.
* * * * *